United States Patent [19]

Clader et al.

[11] Patent Number: 5,238,950

[45] Date of Patent: Aug. 24, 1993

[54] INHIBITORS OF PLATELET-DERIVED GROWTH FACTOR

[75] Inventors: John W. Clader, Cranford; Harry R. Davis, Berkeley Heights, both of N.J.; Deborra Mullins, New York, N.Y.; Stuart Rosenblum, West Orange; Jay Weinstein, Upper Montclair, both of N.J.

[73] Assignee: Schering Corporation, Kenilworth, N.J.

[21] Appl. No.: 808,997

[22] Filed: Dec. 17, 1991

[51] Int. Cl.$^5$ ..................... A61K 31/40; C07D 209/48
[52] U.S. Cl. .................................... 514/360; 514/246; 544/180; 548/427; 548/451; 548/475; 548/477
[58] Field of Search ............... 548/427, 451, 475, 477; 514/360, 246; 544/180

[56] References Cited

U.S. PATENT DOCUMENTS 3,801,533  4/1974  Tetenbaum et al. .................. 524/94
4,194,982  3/1980  Chou ................................... 252/475
4,266,078  5/1981  Pallos .................................. 564/91

OTHER PUBLICATIONS

Lukovits, Chemical Abstract, vol. 110(111, 1988, #87980f).
Soai, et al., *Bull. Chem. Soc. Jpn.*, 55 1982) 1671-1672.
Ferns, et al., *Science*, 253 (1991) 1129-1132.

*Primary Examiner*—Mukund J. Shah
*Assistant Examiner*—Y. N. Gupta
*Attorney, Agent, or Firm*—Paul A. Thompson; Anita W. Magatti

[57] ABSTRACT

A method of inhibiting the binding of PDGF using compounds of the formula I

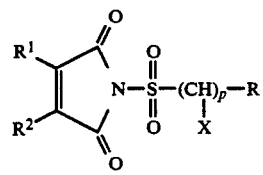

useful in the treatment of atherosclerosis, cancer, retinal detachment, pulmonary fibrosis, arthritis, psoriasis and glomerulonephritis, and restenosis following angioplasty or vascular surgery is disclosed.

Also disclosed are pharmaceutical compositions and novel PDGF inhibitory compounds of the formula

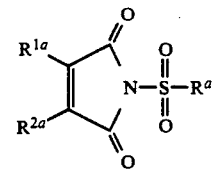

or a pharmaceutically acceptable addition salt thereof, useful in the treatment of atherosclerosis, cancer, retinal detachment, pulmonary fibrosis, arthritis, psoriasis and glomerulonephritis, and restenosis following angioplasty or vascular surgery.

12 Claims, No Drawings

INHIBITORS OF PLATELET-DERIVED GROWTH FACTOR

BACKGROUND OF THE INVENTION

The present invention relates to a method of inhibiting the binding of platelet-derived growth factor (PDGF) using N-alkyl- and N-aryl-sulfonyl phthalimides, maleimides and heterodicarboxamides.

The invention also relates to certain N-alkyl- and N-arylsulfonyl phthalimides, maleimides and heterodicarboxamides useful as inhibitors of PDGF.

Furthermore, the invention relates to a pharmaceutical composition comprising an N-alkyl- or N-aryl-sulfonyl phthalimide, maleimide or heterodicarboxamide useful as an inhibitor of PDGF.

The platelet-derived growth factors (PDGF) are a family of polypeptide mitogens, produced by a variety of different cell types, which stimulate the proliferation of most mesenchymal cells and possibly certain epithelial and endothelial cells. PDGF binds to specific cell surface receptors which possess intrinsic tyrosine kinase activity. Binding of PDGF activates the kinase activity, thereby initiating a cascade of biochemical events culminating in cell division. PDGF cell division can occur by a paracrine mechanism, in which PDGF produced by one cell stimulates the division of other cells, or by an autocrine mechanism, in which a cell stimulates its own division by endogenous production of PDGF.

A compound which inhibits the binding PDGF to its receptor blocks the biological activity of the growth factor. This biological activity includes vascular cell proliferation in atherosclerosis or restenosis following angioplasty or vascular surgery, and division of certain tumor cells, fibroblasts, mesangial cells and epidermal cells. PDGF is also a potent chemotactic agent, stimulating infiltration of macrophages into arterial tissue in atherosclerosis and into the glomerulus in glomerulonephritis. PDGF is also involved in the elaboration of extracellular matrix proteins by retinal pigment epithelial cells, indirectly leading to retinal detachment and blindness. Therefore, a PDGF inhibitor should be useful in the treatment of a variety of diseases, including atherosclerosis, cancer, retinal detachment, pulmonary fibrosis, arthritis, psoriasis and glomerulonephritis, and for blocking the smooth muscle cell hyperplasia which occurs in transplant atherosclerosis and following angioplasty or vascular surgery.

SUMMARY OF THE INVENTION

The method of inhibiting the binding of platelet-derived growth factor (PDGF) of the present invention comprises treating a mammal in need of such treatment with a inhibitory effective does of a compound of the formula I

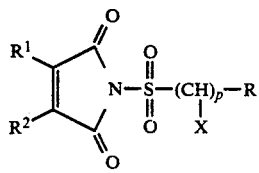

or a pharmaceutically acceptable addition salt thereof, wherein p is 0,1, 2,3,4,5, or 6 and R is hydrogen or an aryl group substituted by 1-5 substitutents $R^4$, provided that R is not hydrogen when p=0;

$R^1$ and $R^2$ are independently selected from the group consisting of hydrogen, $C_1$-$C_8$ alkyl, aryl, cyano and —NHS(O)$_2$alkyl; or $R^1$ and $R^2$ taken together comprise a fused ring of the formula

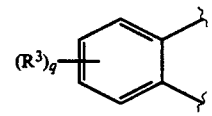

or

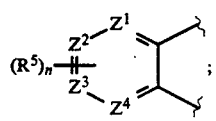

n is 0, 1, 2 or 3;

q is 0, 1, 2, 3 or 4;

$Z^1$, $Z^2$, $Z^3$ or $Z^4$ are independently nitrogen or carbon, provided that at least one of $Z^1$, $Z^2$, $Z^3$ or $Z^4$ is nitrogen;

X, $R^3$ and $R^5$ are independently selected from the group consisting of hydrogen, halogeno, hydroxy, $C_1$-$C_8$ alkyl, $C_1$-$C_8$ alkenyl, $C_1$-$C_8$ alkynyl, $C_1$-$C_8$ alkoxy, aryloxy, amino, alkylamino, dialkylamino, arylamino, diarylamino, trialkylammonium, thio, —S(O)$_2R^6$, —S(O)$_mR^7$, —SO$_3$, nitro, —NHS(O)$_2$alkyl, carboxyl, alkoxycarbonyl, carboxamido, N-alkylcarboxamido, N,N-dialkylcarboxamido, alkylcarbonylamino, arylcarbonylamino, alkylaminocarbonyloxy, alkoxycarbonyloxy, alkylcarbonyloxy, trifluoromethyl, cyano, aryl, heteroaryl, and substituted aryl and substituted heteroaryl, wherein the substituents are 1-5 groups $R^4$; and wherein the $R^4$ substituents are independently selected from the group consisting of hydrogen, halogeno, $C_1$-$C_8$ alkenyl, $C_1$-$C_8$ alkynyl, hydroxy, $C_1$-$C_8$ alkyl, Y-substituted alkyl, $C_1$-$C_8$ alkoxy, aryloxy, amino, alkylamino, dialkylamino, arylamino, diarylamino, trialkylammonium, thio, —SO$_2R^6$, —S(O)$_mR^7$, —SO$_3$, nitro, carboxyl, alkoxycarbonyl, benzyloxycarbonyl, alkenyloxycarbonyl, carboxamido, N-phthalimido, cyanoalkoxycarbonyl, carboxyalkoxycarbonyl, benzyloxycarbonylalkoxycarbonyl, N-alkylcarboxamido, N,N-dialkylcarboxamido, trifluoromethyl, cyano, aryl and heteroaryl; and Y is selected from the group consisting of halogeno, trialkylammonium, amino, carboxy, pyridinium, triarylphosphonium, benzyloxycarbonyl, hexamethylenetetraminium, —N═CH—alkyl, —N═CH—aryl and —N═CH—N(alkyl)$_2$,;

$R^6$ is amino, arylamino, alkylamino or dialkylamino;

$R^7$ is $C_1$-$C_8$ alkyl or aryl; and m is 0, 1 or 2.

This invention also relates to novel PDGF inhibitory compounds of the formula Ia

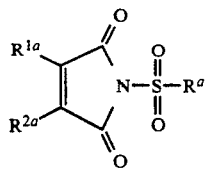

or a pharmaceutically acceptable addition salt thereof, wherein $R^a$ is an aryl group substituted by 1-5 substituents $R^{4a}$;

$R^{1a}$ and $R^{2a}$ are independently selected from the group consisting of aryl, cyano and —NHS(O)$_2$alkyl; or $R^{1a}$ and $R^{2a}$ together comprise a fused ring of the formula

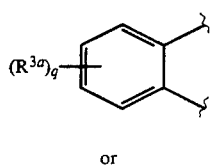

or

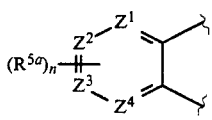

n is 0, 1, 2 or 3;
q is 0, 1, 2, 3 or 4;
$Z^1$, $Z^2$, $Z^3$ or $Z^4$ are independently nitrogen or carbon, provided that at least one of $Z^1$, $Z^2$, $Z^3$ or $Z^4$ is nitrogen;

$R^{3a}$ and $R^{5a}$ are independently selected from the group consisting of hydroxy, C$_1$-C$_8$ alkyl, C$_1$-C$_8$ alkenyl, C$_1$-C$_8$ alkynyl, C$_1$-C$_8$ alkoxy, aryloxy, arylamino, diarylamino, trialkylammonium, thio, —S(O)$_2$R$^6$, —S(O)$_m$R$^7$, —SO$_3$, nitro, —NHS(O)$_2$alkyl, carboxyl, alkoxycarbonyl, carboxamido, N-alkylcarboxamido, N,N-dialkylcarboxamido, arylcarbonylamino, alkylaminocarbonyloxy, alkoxycarbonyloxy, alkylcarbonyloxy, trifluoromethyl, cyano, aryl, heteroaryl, and substituted aryl and substituted heteroaryl, wherein the substituents are 1-5 groups $R^{4a}$; and wherein the $R^{4a}$ substituents are independently selected from the group consisting of C$_1$-C$_8$ alkenyl, C$_1$-C$_8$ alkynyl, hydroxy, Y-substituted alkyl, alkylamino, dialkylamino, arylamino, diarylamino, trialkylammonium, thio, —S(O)$_m$R$^7$, —SO$_3$, carboxyl, alkoxycarbonyl, benzyloxycarbonyl, alkenyloxycarbonyl, carboxamido, N-phthalimido, cyanoalkoxycarbonyl, carboxyalkoxycarbonyl, benzyloxycarbonylalkoxycarbonyl, N,N-dialkylcarboxamido, trifluoromethyl, cyano and heteroaryl; and Y is selected from the group consisting of halogeno, trialkylammorium, amino, carboxy, pyridinium, triarylphosphonium, benzyloxycarbonyl, hexamethylenetetraminium, —N=CH—alkyl, —N=CH—aryl and —N=CH—N(alkyl)$_2$;

$R^7$ is C$_1$-C$_8$ alkyl or aryl; and
m is 0, 1 or 2.

The following groups of compounds of the formula I are preferred for use in the method of this invention.

Compounds of the formula I wherein p=0 and R is phenyl or naphthyl, substituted by 1-5 substituents $R^4$.

Compounds of the formula I wherein p=1-6, X is hydrogen and R is phenyl or naphthyl, substituted by 1-5 substituents $R^4$.

Compounds of the formula I wherein $R^1$ and $R^2$ together comprise a fused ring of the formula

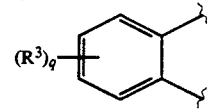

and wherein $R^3$ is selected from the group consisting of hydrogen, halogeno, nitro and amino.

Compounds of the formula I wherein $R^1$ and $R^2$ together comprise a fused ring of the formula

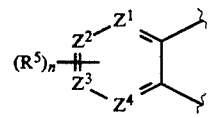

wherein $Z^1$ and $Z^4$ are each nitrogen and n=0.

The following groups of compounds of formula I are more preferred for use in the method of this invention:
compounds of the formula

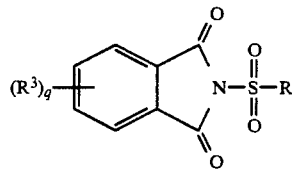

wherein: $R^3$ is selected from the group consisting of hydrogen, halogeno, nitro and amino; and R is phenyl or naphthyl, substituted by 1-5 substituents $R^4$; and
compounds of the formula

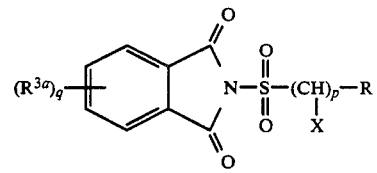

wherein: X is hydrogen; p=1-6; $R^3$ is selected from the group consisting of hydrogen, halogeno, nitro and amino; and R is phenyl or naphthyl, substituted by 1-5 substituents $R^4$.

The following groups of compounds of formula I are especially preferred for use in the method of this invention:
compounds of the formula

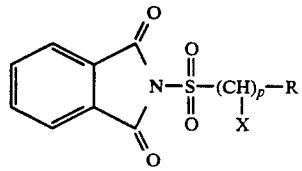

wherein: X is hydrogen; p=1-6; R is phenyl or naphthyl, substituted by 1-5 substituents $R^4$; and $R^4$ is selected from the group consisting of hydrogen, halogeno, nitro, Y-substituted alkyl, amino, alkylamino, dialkylamino, and alkoxycarbonyl; and compounds of the formula

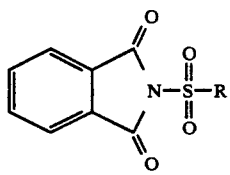

wherein: R is phenyl or naphthyl, substituted by 1-5 substituents $R^4$ $R^4$ is selected from the group consisting of hydrogen, halogeno, nitro, Y-substituted alkyl, amino, alkylamino, dialkylamino, alkoxycarbonyl, benzyloxycarbonyl, and alkoxyalkoxycarbonyl; and Y is halogeno, benzyloxycarbonyl or triphenylphosphonium.

Preferred compounds of formula Ia are those wherein $R^{1a}$ and $R^{2a}$ together comprise a fused ring of the formula

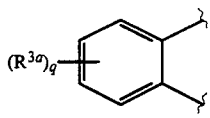

Also preferred are compounds of formula Ia wherein $R^{1a}$ and $R^{2a}$ together comprise a fused ring of the formula

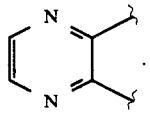

Another group of preferred compounds of the formula Ia is that wherein $R^a$ is phenyl or naphthyl, substituted by 1-5 group $R^{4a}$.

More preferred are compounds of the formula Ia wherein $R^{1a}$ and $R^{2a}$ together comprise a fused ring of the formula

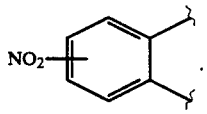

Another group of more preferred compounds of the formula Ia is that wherein $R^a$ is phenyl or naphthyl, substituted by 1-5 groups $R^{4a}$ and $R^{4a}$ is selected from the group consisting of Y-substituted alkyl, alkylamino, dialkylamino or alkoxycarbonyl.

Especially preferred are compounds of the formula Ia wherein $R^a$ is phenyl or naphthyl, substituted by 1-5 groups $R^{4a}$, $R^{4a}$ is selected from the group consisting of Y-substituted alkyl, alkylamino, dialkylamino or alkoxycarbonyl, and Y is halogeno, benzyloxycarbonyl or triphenylphosphonium.

This invention also relates to pharmaceutical compositions comprising a PDGF inhibitor of formula Ia in a pharmaceutically acceptable carrier.

DETAILED DESCRIPTION

As used herein, the term "alkyl" means straight or branched alkyl chains of 1 to 8 carbon atoms, and "alkoxy" similarly refers to alkoxy groups having 1 to 8 carbon atoms.

"Halogeno" means fluorine, chlorine, bromine or iodine radicals.

"Aryl" means mono-cyclic or fused ring bicyclic carbocyclic aromatic groups having 6 to 10 ring members and "heteroaryl" means mono-cyclic or fused ring bicyclic aromatic groups having 5-10 ring members wherein 1-3 ring members are independently nitrogen, oxygen or sulfur. In substituted aryl and heteraryl groups the carbon ring members are substituted by one to five substituents $R^4$. Examples of aryl groups are: phenyl and napthyl. Examples of heteroaryl groups are: pyridyl, pyrimidinyl, pyrazinyl, pyrrolyl, triazinyl, imidazolyl, furanyl, and thienyl.

Compounds of the formula Ia are a subgenus of compounds of the formula I, therefore all compounds of formula Ia are also compounds of formula I.

Certain compounds of the invention e.g., those with a basic amino group, also form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from the respective salt forms somewhat in certain physical properties, such as solubility in polar solvents, but the salts are otherwise equivalent to their respective free base forms for purposes of this invention.

Certain compounds of the invention are acidic e.g., those compounds which possess a carboxyl group. These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

The salts may be formed by conventional means, as by reacting the free acid or base form of the product with one or more equivalents of the appropriate base or acid, respectively, in a solvent or medium in which the salt is insoluble, or in a solvent such as water which is then removed in vacuo or by freeze-drying or by exchanging the cations of an existing salt for another cation on a suitable ion exchange resin.

Compounds of the present invention can be prepared using methods well known to those skilled in the art. For example, compounds of the formula I can be prepared via the following methods.

In a method for preparing compounds of the formula I, wherein p is 1, 2, 3, 4, 5 or 6, a bromide of the formula V is converted to the grignard reagent by treatment with Mg, then reacted with $SO_2$. The resulting magenesium sulfinate salt is treated with sulfuryl chloride to form a sulfonyl chloride of the formula VI. Sulfonyl chloride VI is then reacted with a dicarboximide of the formula VII to form a compound of the formula I, wherein p is 1, 2, 3, 4, 5 or 6.

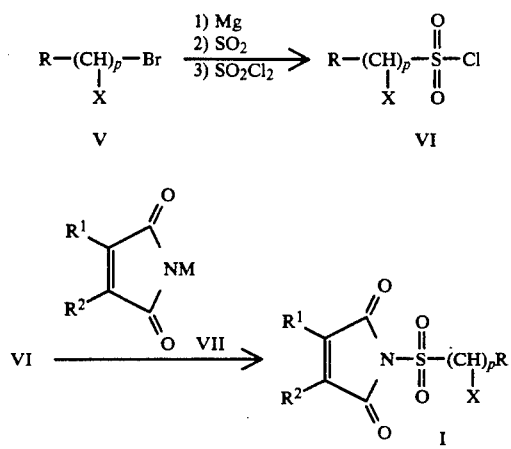

Starting bromides of formula V and dicarboximides of formula VII are commercially available or can be prepared by well known methods.

In a method for preparing compounds of the formula Ib, i.e., compounds of formula I wherein p=0 and R is an aryl group substituted by 1-5 substituents $R^4$, an amine of the formula II, wherein $R^b$ is an aryl group as defined above, is converted to the analogous sulfonamide III. Reaction of the sulfonamide III with a diacid chloride derivative of the formula IV gives the desired sulfonyldicarboximide Ib.

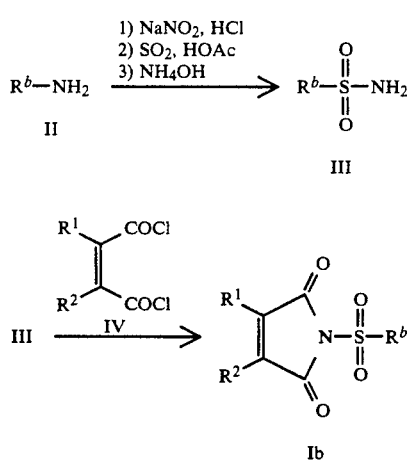

Starting amines of the formula II are commercially available or readily prepared by well known methods. Diacid chlorides of the formula IV are either commercially available or can be prepared from the corresponding diacids VIII by treatment with a suitable chlorinating agent, such as oxalkyl chloride or thionyl chloride. The diacids of the formula VIII are either commercially available or can be prepared by methods well known to those skilled in the art.

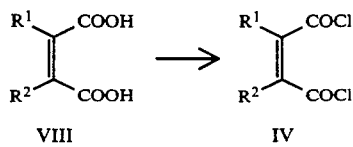

In a method for preparing compounds of the formula Ib, wherein one of the $R^4$ substituents is bromomethyl, a corresponding compound of the formula Ib, wherein one of the $R^4$ substituents is methyl, is treated with N-bromosuccinimide.

In a method for preparing compounds of the formula Ib, wherein and one of the $R^4$ substituents is (trialkylammonium)methyl or (triphenylphosphonium)methyl, a corresponding compound of the formula Ib, wherein one of the $R^4$ substituents is bromomethyl, is treated with a trialkylamine or triphenylphoshpine, respectively.

In the above process, one skilled in the art will appreciate that it is desirable and sometimes necessary to protect the groups in column 1 of Table 1. Conventional protecting groups are operable. Preferred protected groups appear in column 2 of Table 1.

TABLE 1

| PROTECTED GROUPS | |
|---|---|
| 1. GROUP TO BE PROTECTED | 2. PROTECTED GROUP |
| —COOH | —COOalkyl, —COObenzyl, —COOphenyl, ![structure] |
| ⟩NH | ⟩NCOalkyl, ⟩NCObenzyl, ⟩NCOphenyl |
| ⟩CO | ![structures] |
| —OH | ![structure], —OCH₂phenyl, —OCH₃, OSi(CH₃)₂(t-Bu), |
| —NHR, wherein R is any substituent on an amino group within the scope of the claims | ![structure], —NR—CO—CF₃, —NRCOCH₃, —NRCH₂![phenyl] |

TABLE 1-continued
PROTECTED GROUPS

| 1. GROUP TO BE PROTECTED | 2. PROTECTED GROUP |
|---|---|
| —NH₂ | 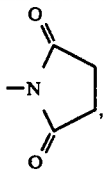 |
| | —NH—C(O)—O(t-Bu) |

Of course other protecting groups well known in the art may be used. After the reaction of reactions, the protecting groups may be removed by standard procedures well known in the art.

We have found that the compounds of formula I are inhibitors of PDGF and thus block the biological activity of PDGF. Therefore, the compounds of this invention are useful in the treatment of the various diseases, described above, in which PDGF activity plays a role.

In addition to the compound aspect, the present invention therefore also relates to a method of treating the aforementioned diseases. The compound is preferably administered in a pharmaceutically acceptable carrier suitable for oral administration.

The in vitro activity of compounds of formula I can be determined by the following procedure.

PDGF Receptor Binding Assay

The ability of a compound of the present invention to prevent binding of PDGF to the PDGF receptor can be determined using the following method.

Seed $1.5 \times 10^4$ human foreskin fibroblasts (HSF) in 24 well dishes in growth medium [Dulbecco's Modified Eagle's Medium (DMEM)+10% fetal bovine serum+2 mM glutamine+penicillin (50 U/mL)/streptomycin (50 μg/mL)] and grow to approximately 70% confluence. Remove the growth medium by aspiration and wash the HSF one or two times in 1 mL of phosphate-buffered saline. Replace the medium with 1 mL of DMEM+2% equine plasma-derived serum (PDGF deficient)+2 mM glutamine+penicillin (50 U/mL) streptomycin (50 μg/mL) and incubate for 48 hours.

The receptor binding assay is carried out at 4° C. using ice-cold solutions unless otherwise noted, and all samples should be in duplicate.

Incubate the cells for 4 hours in the presence of 0, 1, 2, 4, 16, 32 or 200 ng of recombinant human c-sis (PDGF B chain homodimer) and 0.2 ng of $^{125}$I labelled c-sis. Solubilize the cells, then count the samples in a gamma counter. The concentration of PDGF in an unknown is determined by ascertaining the amount of unlabeled c-sis which must be added to the cells to give the number of counts in the unknown.

A working solution of the unlabeled c-sis used in the above procedure is prepared as follows. Prepare a stock solution of 1 mg/ml in 1M acetic acid, 0.15M NaCl. Add 1 μL (1 μg) of the stock solution to 99 μL of DMEM containing 2 mg/ml gelatin. Make a 1:10 dilution to obtain a working dilution of 1 ng/μL.

The present invention also relates to a pharmaceutical composition comprising a compound of formula I of this invention and a pharmaceutically acceptable carrier. The compounds of formula I can be administered in any conventional oral dosage form such as capsules, tablets powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible fillers, binders, disintegrnts, buffers, preservatives, anti-oxidants, lubricants, flavorings, thickeners, coloring agents, emulsifiers and the like.

The following are illustrative examples of preparing compounds of the formula I.

Preparation 1

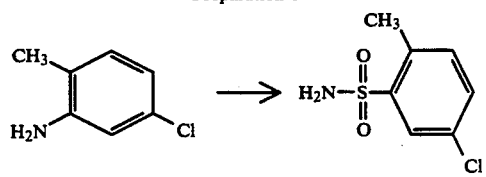

Prepare a solution of 2-methyl-5-chloroaniline (10 g) in 150 mL of concentrated HCl. Add 75 g of ice followed by a cold solution of sodium nitrite (21 g) in 30 mL of water. Stir the mixture at 0° C. for one hour, then add the mixture to a 30% solution of sulfur dioxide in glacial acetic acid. Immediately add a solution of cuprous chloride dihydrate (12 g) in 21 mL water. Stir the mixture at 0° C. for two hours. Filter the solids, then extract the filtrate with diethyl ether. Concentrate the ether extract, under vacuum, to a residue. Combine the residue and the filtered solids, then dissolve in concentrated aqueous ammonia and stir the solution overnight at ambient temperature. Filter the resulting mixture, then concentrate the filtrate until crystallization begins. Cool the filtrate, then collect the solids by filtration to give 16 grams of the title compound.

Preparation 2

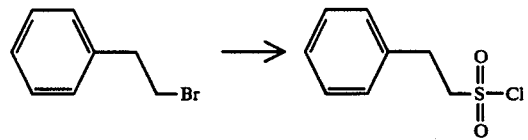

Combine 1.28 g of magnesium turnings and 10 mL diethyl ether, then add 6.0 mL of phenethylbromide at a rate sufficient to maintain the solvent at gentle reflux. When addition of the bromide is complete, stir the mixture for 0.5 h, then cool to −10° C. Bubble sulfur dioxide into the mixture until the sulfinate salt precipitates. Remove the solvent under vacuum and suspend the solid residue in 20 mL methylene chloride. Cool the suspension to 0° C., then slowly add sulfuryl chloride (100 mole %). Allow the mixture to warm to 22° C. and stir for 0.5 h. Wash with 10 mL water, dry the organic solution over MgSO₄, then remove the solvent under vacuum to give 8.3 g of the title compound.

EXAMPLE 1

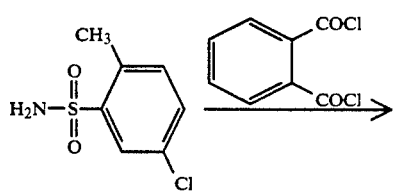

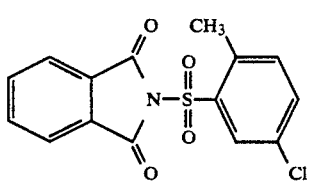

Dissolve the product of Preparation 1 (10 g) in 30 mL of toluene and add 10 g phthaloyl chloride. Heat the mixture at reflux overnight, allow the mixture to cool to room temperature, then filter to obtain 12 g of the title compound, m.p. 203°–205° C.

The following compounds were prepared by substantially the same procedure:

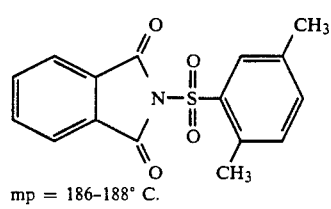
mp = 186–188° C.
Example 1A

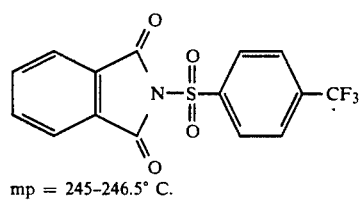
mp = 245–246.5° C.
Example 1B

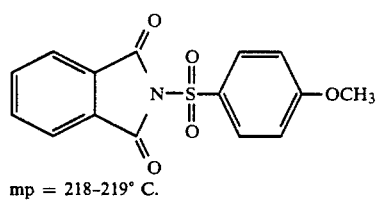
mp = 218–219° C.
Example 1C

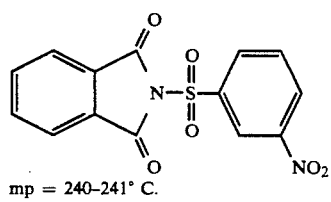
mp = 240–241° C.
Example 1D

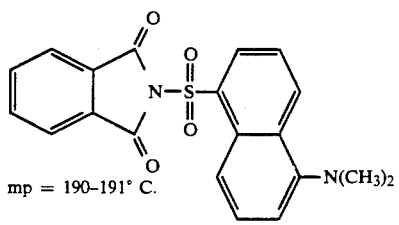
mp = 190–191° C.
Example 1E

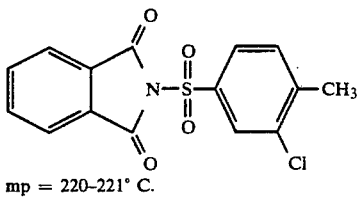
mp = 220–221° C.
Example 1F

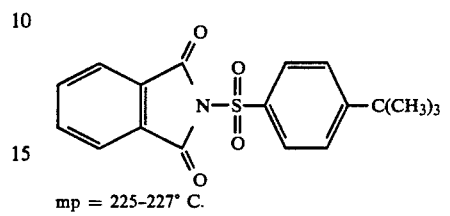
mp = 225–227° C.
Example 1G

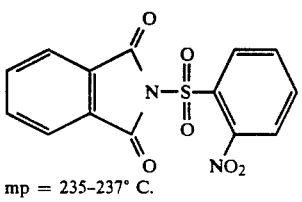
mp = 235–237° C.
Example 1H

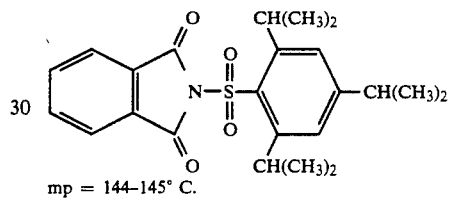
mp = 144–145° C.
Example 1I

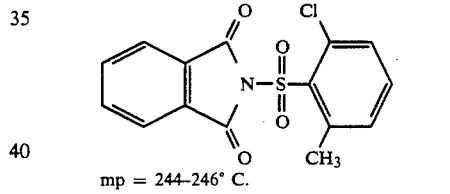
mp = 244–246° C.
Example 1J

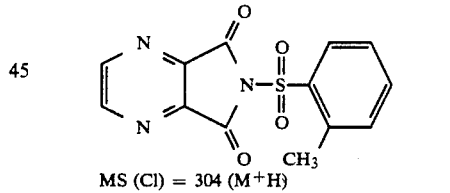
MS (CI) = 304 (M+H)
Example 1K

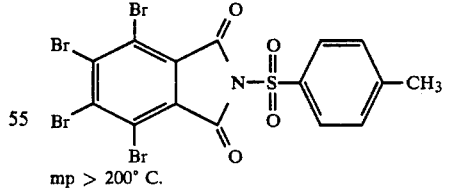
mp > 200° C.
Example 1L

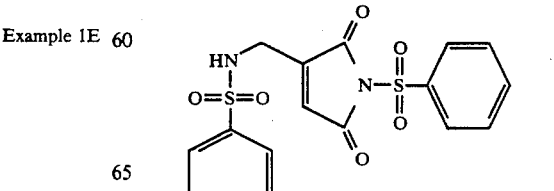
MS (CI) = 409 (M+H)
Example 1M

-continued
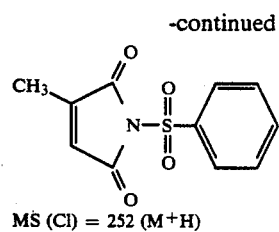
MS (CI) = 252 (M+H)
Example 1O
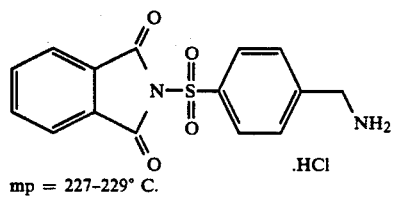
mp = 227-229° C.
Example 1P
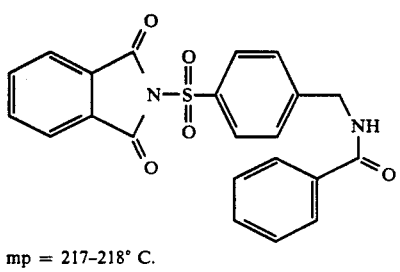
mp = 217-218° C.
Example 1Q
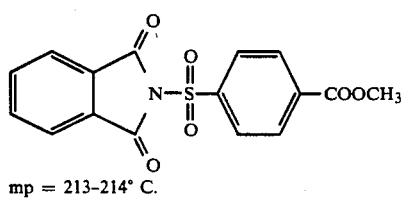
mp = 213-214° C.
Example 1R
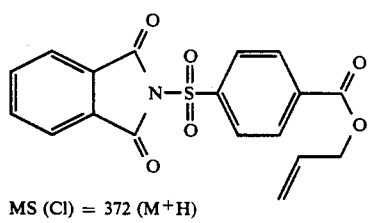
MS (CI) = 372 (M+H)
Example 1S
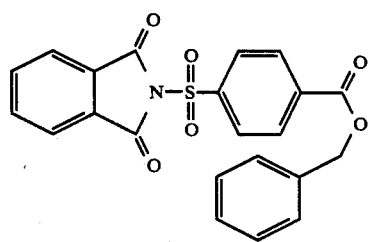
MS (CI) = 422 (M+H)
Example 1T
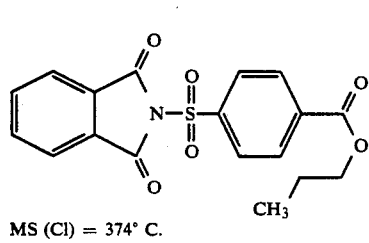
MS (CI) = 374° C.
-continued
Example 1N
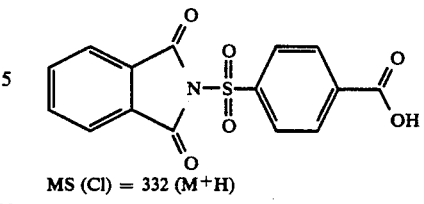
MS (CI) = 332 (M+H)
Example 1U
Example 1V
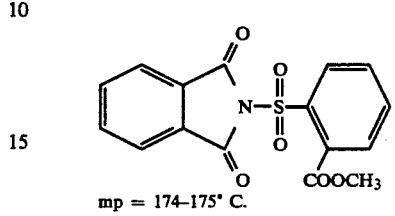
mp = 174-175° C.
Example 1W
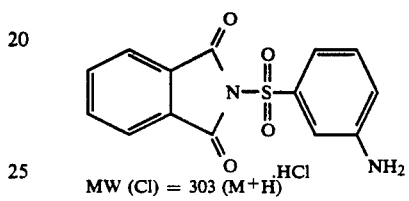
MW (CI) = 303 (M+H) HCl
Example 1X
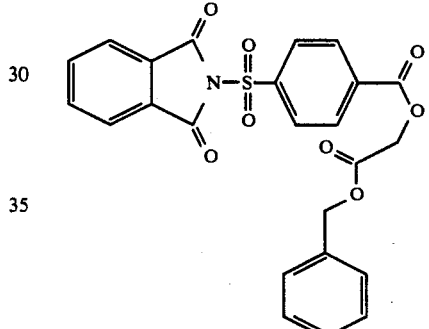
MS (CI) = 481 (M+H)
Example 1Y
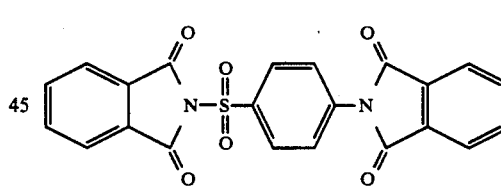
mp = 188-190° C.
Example 1Z
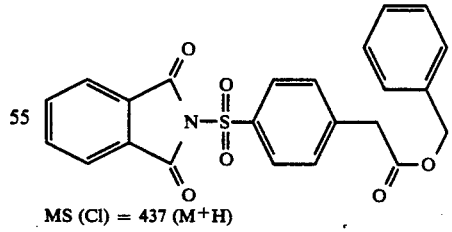
MS (CI) = 437 (M+H)
Example 1AA
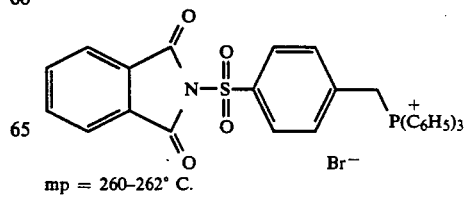
mp = 260-262° C.

-continued
Example 1BB
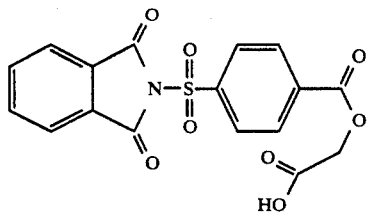
MS (CI) = 389 (M+H)
Example 1CC
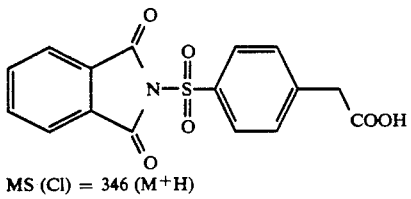
MS (CI) = 346 (M+H)
Example 1DD
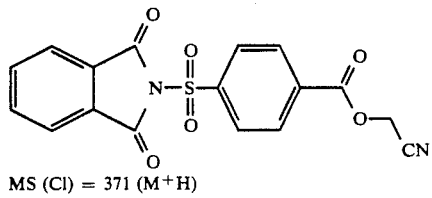
MS (CI) = 371 (M+H)
Example 1EE
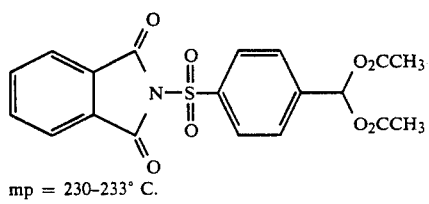
mp = 230–233° C.
Example 1FF
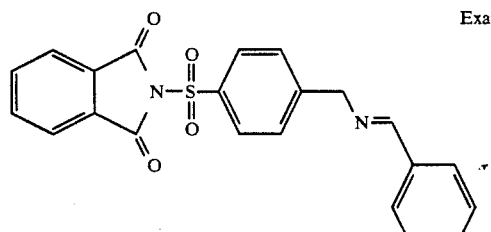
MS (CI) = 405 (M+H)
Example 1GG
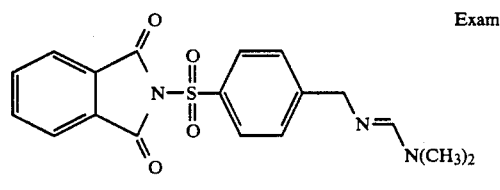
mp = 265–267° C.
Example 1HH
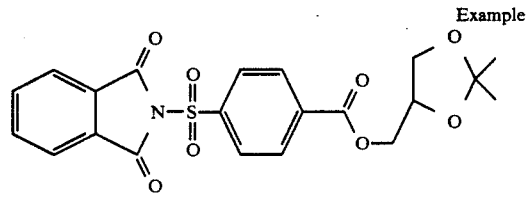
MS (CI) = 446 (M+H)
-continued
Example 1II
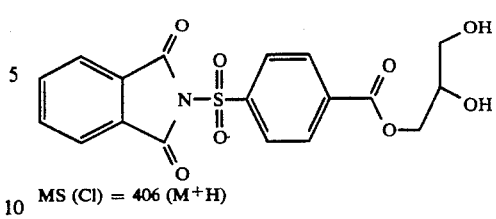
MS (CI) = 406 (M+H)
Example 1JJ
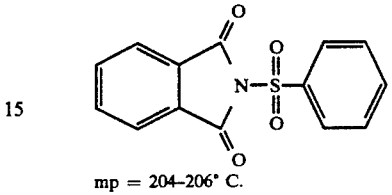
mp = 204–206° C.
Example 1KK
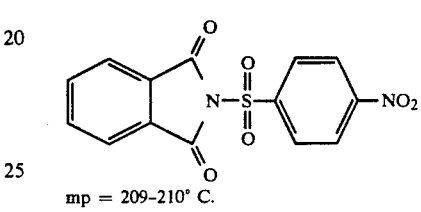
mp = 209–210° C.
Example 1LL
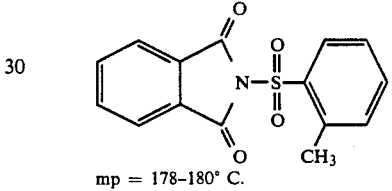
mp = 178–180° C.
Example 1MM
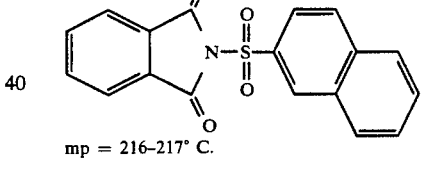
mp = 216–217° C.
Example 1NN
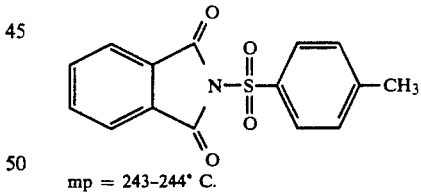
mp = 243–244° C.
Example 1OO
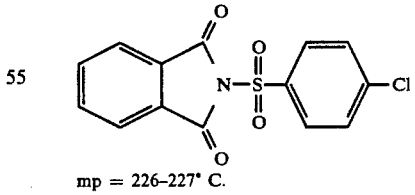
mp = 226–227° C.
Example 1PP
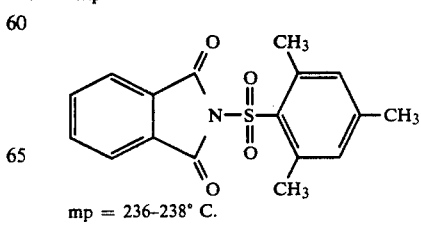
mp = 236–238° C.

Example 1QQ

[Structure: phthalimide-N-SO2-phenyl-CH3 (meta)]
mp = 202–203° C.

EXAMPLE 2

[Structure: phthalimide-N-SO2-(2-CH3, 5-Cl-phenyl) → phthalimide-N-SO2-(2-CH2Br, 5-Cl-phenyl)]

Dissolve the product of Example 1 (15 g) and N-bromosuccinimide (19 g) in 400 mL tetrachloromethane, and heat the solution at reflux for 12 hours. Cool the solution then wash with NaHSO₃ (aqueous), then three times with water. Dry the organic solution over Na₂SO₄, filter, then evaporate the solvent to a solid residue. Recrystallize the residue from CH₂Cl₂ to give the title compound, m.p. 164° C.

The following compounds were prepared by substantially the same procedure from suitable starting materials, but adding a trace (0.05 g) of benzoyl peroxide to the reaction mixture when solubility of the starting material is low:

Example 2A
[Structure with Cl and CHBr2 substituents]
mp = 190° C. (dec.)

Example 2B
[Structure with CH2Br substituent]
mp = 214–215° C.

Example 2C
[Structure with CH2Br and Cl substituents]
mp = 251–252° C.

Example 2D
[Structure: phthalimide-N-SO2-phenyl-CHBr2]
mp = 190° C. (dec.)

Example 2E
[Structure: phthalimide-N-SO2-phenyl-CH2Br (meta)]
mp = 209–210° C.

Example 2F
[Structure: phthalimide-N-SO2-phenyl-CH2Br (para)]
mp = 229–231° C.

EXAMPLE 3

[Structure: phthalimide-N-SO2-phenyl-CH2-N(Et)3(+) Br(−)]

Combine the product of Example 5(5.2g), 2.2 ml (120 mol%) triethyl amine and 15 ml methylene chloride and heat the mixture at reflux. After 2 h, filter to collect the precipitate and the cool the filtrate overnight at −10° C. Filter to collect the second crop of product. Dry the combined product fractions in vacuo to afford 5.65 g (86%) of the title compound.

Anal. Calcd. for $C_{21}H_{25}N_2O_4SBr$: C, 52.39;H,5.20;N,5.82;

Found: C,52.07;H,5.38;N,5.80.

The following compounds were prepared by substantially the same procedure:

Example 3A
[Structure: phthalimide-N-SO2-phenyl-CH2-N(+)pyridinium Br−]
mp = 261–263° C.

Example 3B

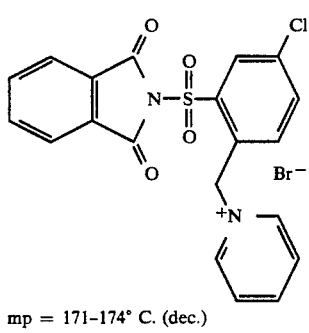

mp = 171–174° C. (dec.)

Example 3C

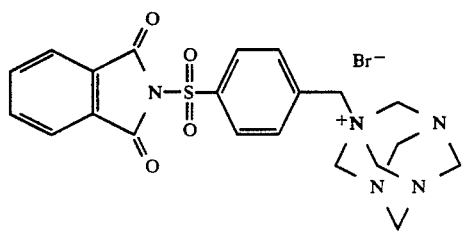

FAB MS (M⁺ − Br) = 440

Example 3D

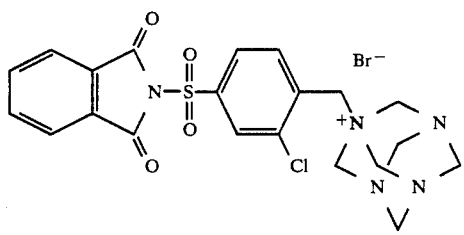

FAB MS (M⁺ − Br) = 474

Example 3E

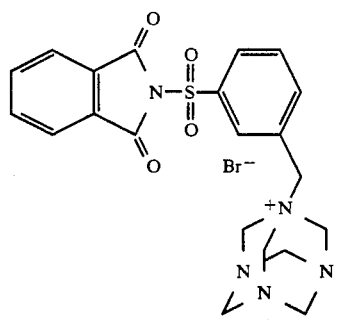

FAB MS (M⁺ − Br) = 440

EXAMPLE 4

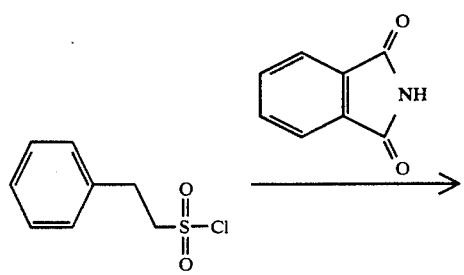

-continued

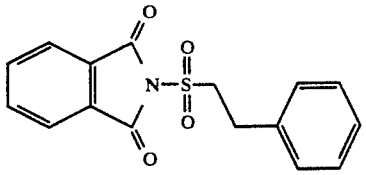

Combine the sulfonyl chloride of Preparation 2 (3.2 g), phthalimide (2.3 g) and 50 mL of methylene chloride. Add 10 mL of 40% tetrabutylammonium hydroxide (aqueous) and stir the biphasic mixture while heating to 60° C. After stirring at 60° C. for 3–5 h, cool the mixture and separate the organic phase. Wash the organic solution with 10 mL of 1N HCl (aqueous), then with 10 mL water. Dry the organic solution over MgSO₄ then concentrate to a residue. Purify the residue on silica gel (1:1 hexane/ethyl acetate) to give 1.47 g of the title compound, mp=165°–166° C.

The following compounds were prepared by substantially the same procedure:

Example 4A

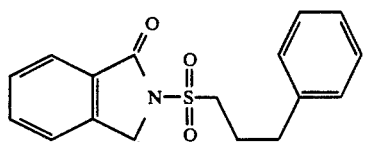

Anal. for $C_{17}H_{15}NO_4S$:
calc.: C, 62.00; H, 4.56; N, 4.25
found: C, 62.41; H, 4.32; N, 4.40

Example 4B

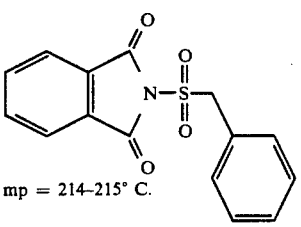

mp = 214–215° C.

Example 4C

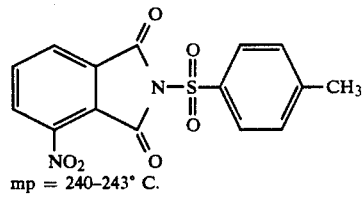

mp = 240–243° C.

Example 4D

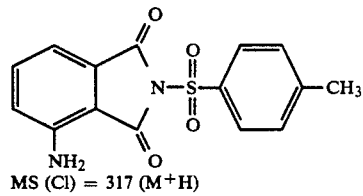

MS (CI) = 317 (M⁺H)

Example 4E

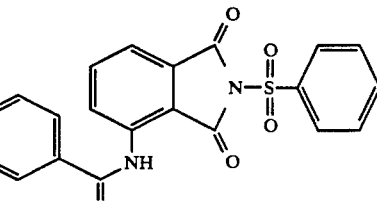

mp > 250° C.

Example 4F

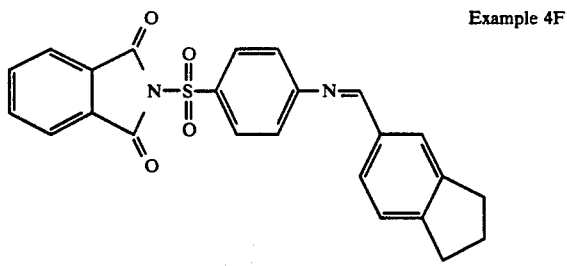

mp = 240–245° C. (dec.)

Example 4G

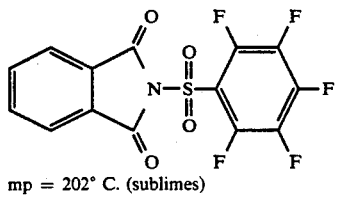

mp = 202° C. (sublimes)

Example 4H

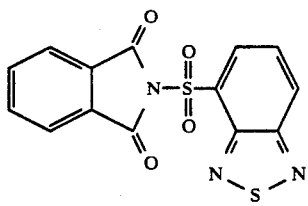

mp = 242–243° C.

Example 4I

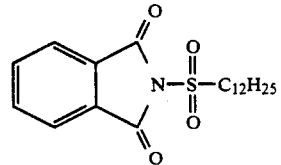

mp = 127–128° C.

Example 4J

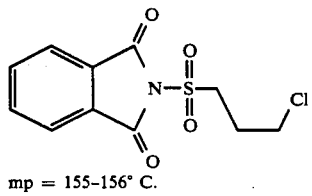

mp = 155–156° C.

Example 4K

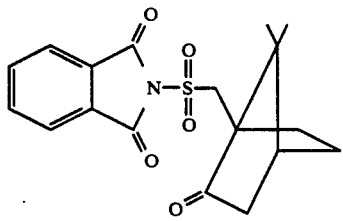

mp = 159–160° C.

Example 4L

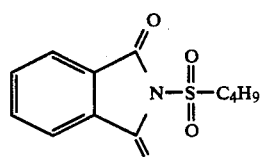

mp = 120–122° C.

Example 4M

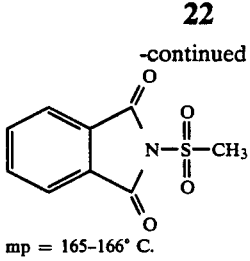

mp = 165–166° C.

Using the methods described above, the following in vitro data were obtained for the preferred compounds, which are identified in the following tables by the corresponding example numbers.

| Example # | Binding IC50 | Example # | Binding IC50 |
|---|---|---|---|
| 1 | 3 | 1A | 4 |
|   | 14 |    | 4.2 |
| 1B | 1.8 | 1C | 3 |
|    | 10.3 |    | >10 |
|    | 9.1 |    |    |
| 1D | 3 | 1E | 1 |
|    |   |    | 0.8 |
|    |   |    | 1.6 |
| 1F | 2 | 1G | 5 |
|    | 2 |    | 7.2 |
| 1H | 3 | 1I | 4.8 |
|    | 0.5 |    | 4.1 |
| 1J | 24.5 | 1K | 100 |
|    | 75 |    |    |
| 1L | 4.3 | 1M | 3 |
|    | 4.7 |    | 6 |
| 1N | 3 | 1O | 10 |
|    | >10 |    | >100 |
| 1P | <1 | 1Q | 4.4 |
|    | 0.1 |    | 4.9 |
| 1R | 0.5 | 1S | 0.75 |
|    | 0.1 |    | 0.2 |
|    |    |    | 4(4) |
| 1T | 1.0 | 1U | 5.5 |
|    | 0.04 |    |    |
| 1V | 13 | 1W | >100 |
| 1X | 0.1 | 1Y | >100 |
|    | 0.8 |    |    |
|    | 1.0 |    |    |
| 1Z | 1.0 | 1AA | 0.6 |
|    | 1.3 |    | 2.2 |
| 1BB | 30 | 1CC | 15.7 |
|     | 4 |     |     |
|     | 51 |     |     |
| 1DD | 0.7 | 1EE | 5.2 |
|     | 0.7 |     | 8.5 |
| 1FF | 24 | 1GG | >100 |
|     | >100 |     |     |
| 1HH | 1.3 | 1II | 3 |
|     | 1.2 |     | 2.5 |
|     | 5.6 |     | 3.8 |
| 1JJ | 9 | 1KK | 1 |
|     | 30 |     | 3 |
| 1LL | <1 | 1MM | 3 |
|     | >10 |     | 1 |
|     | 3 |     |     |
| 1NN | 7 | 1OO | 7 |
|     |   |     | 6 |
| 1PP | 17 | 1QQ | 5 |
|     | 9 |     |    |
| 2 | 0.7 | 2A | 2 |
|   | 0.3 |    | 5.5 |
|   | 1.3 |    |    |
|   | 0.5 |    |    |
|   | 0.8 |    |    |
|   | 0.1 |    |    |
|   | 0.7 |    |    |
|   | 0.3 |    |    |
|   | 0.7 |    |    |
| 2B | 4.5 | 2C | <1 |
|    | 3.3 |    | 0.6 |
| 2D | 0.3 | 2E | 0.1 |
|    | 0.04 |    | 0.5 |

-continued

| Example # | Binding IC50 | Example # | Binding IC50 |
|---|---|---|---|
| 2F | <1 | 3 | 1.9 |
|  | 1 |  | 9.4 |
|  | 0.7 |  | 40 |
| 3A | 65 | 3B | 40 |
|  | ≈100 |  | >100 |
| 3C | 23.3 | 3D | 2.4 |
|  | 28.8 |  | 1.6 |
| 3E | 7.7 | 4 | 10.3 |
| 4A | 0.8 | 4B | 6.9 |
|  | 13 |  | 21 |
| 4C | 0.7 | 4D | ≈60 |
|  | 0.6 |  |  |
|  | 5.7 |  |  |
|  | 5.2 |  |  |
| 4E | >100 | 4F | >100 |
| 4G | >100 | 4H | 0.04 |
|  |  |  | 0.8 |
| 4I | 1.4 | 4J | 33 |
|  | 56 |  |  |
|  | 28 |  |  |
| 4K | 51 | 4L | 31 |
|  |  |  | 47 |
| 4M | 11 |  |  |
|  | >100 |  |  |
|  | >200 |  |  |

We claim:

1. A compound of the formula

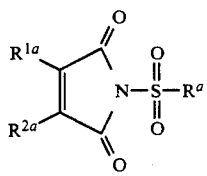

or a pharmaceutically acceptable addition salt thereof, wherein $R^a$ is an aryl group substituted by 1-5 substitutents $R^{4a}$;

$R^{1a}$ and $R^{2a}$ together comprise a fused ring of the formula

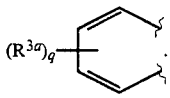

q is 0 or 1
$R^{3a}$ is nitro; and
wherein the $R^{4a}$ substituents are independently selected from the group consisting of hydroxy, Y-substituted alkyl, alkylamino, dialkylamino, arylamino, diarylamino, trialkylammonium, thio, —S(O)$_m$R$^7$, —SO$_3$, carboxyl, alkoxycarbonyl, benzyloxycarbonyl, alkenyloxycarbonyl, carboxamido, N-phthalimido, cyanoalkoxycarbonyl, carboxyalkoxycarbonyl, benzyloxycarbonyl-alkoxycarbonyl, N,N-dialkylcarboxamido, trifluoromethyl and cyano;

Y is selected from the group consisting of halogeno, trialkylammonium, amino, carboxy, pyridinium, triarylphosphonium, benzyloxycarbonyl, hexamethylenetetraminium, —N=CH—alkyl, —N=CH—aryl and —N=CH—N(alkyl)$_2$;

$R^7$ is $C_1$-$C_8$ alkyl or aryl; and
m is 0, 1 or 2.

2. A compound of claim 1 having the structural formula

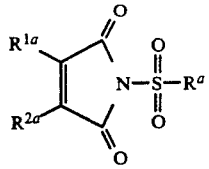

wherein:

| $R^{1a}$, $R^{2a}$ | $R^a$ |
|---|---|
|  | 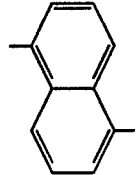 |
|  | —⟨phenyl⟩—CF$_3$ |
| 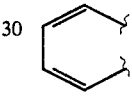 | 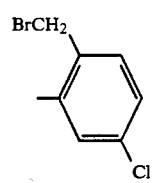 |
| 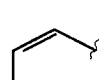 | 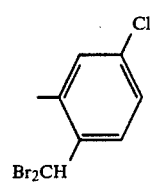 |
| 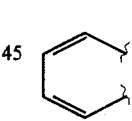 | 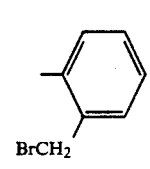 |
| 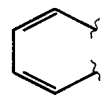 | 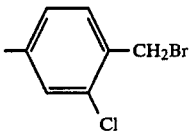 |
| 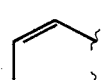 | 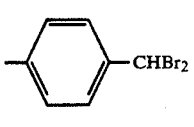 |
| 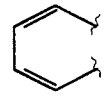 | 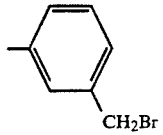 |

-continued
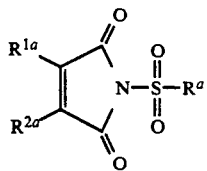
wherein:
| $R^{1a}, R^{2a}$ | $R^a$ |
|---|---|
| 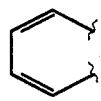 | 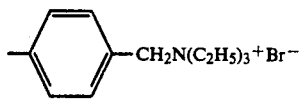 |
| 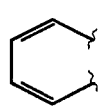 | 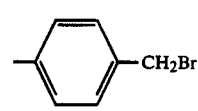 |
| 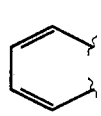 | 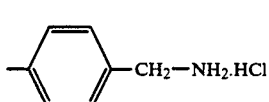 |
|  | 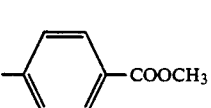 |
|  | 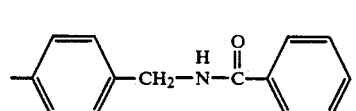 |
|  | 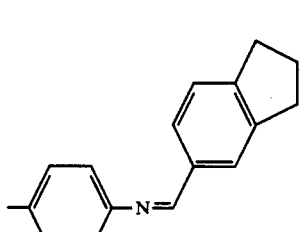 |
|  | 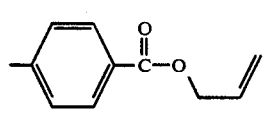 |
|  | 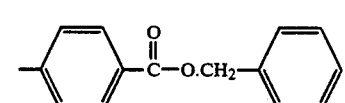 |
| 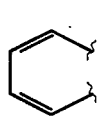 | 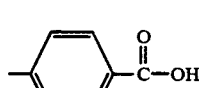 |
|  | 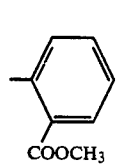 |
-continued
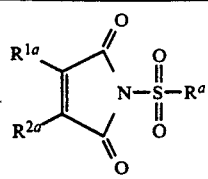
wherein:
| $R^{1a}, R^{2a}$ | $R^a$ |
|---|---|
| 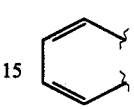 | 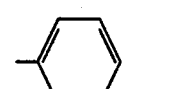 |
| 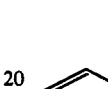 | 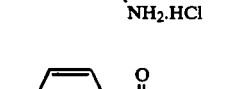 |
| 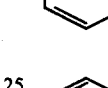 | 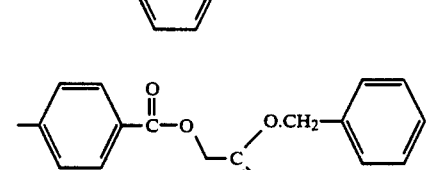 |
| 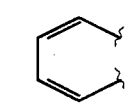 | 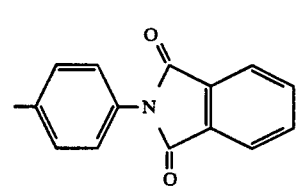 |
|  | 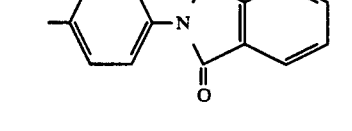 |
| 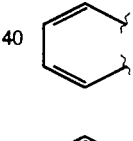 | 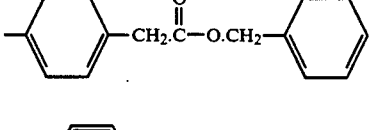 |
| 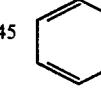 | 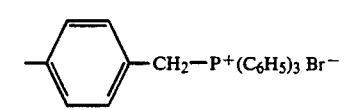 |
| 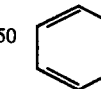 | 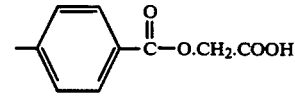 |
| 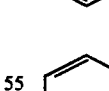 | 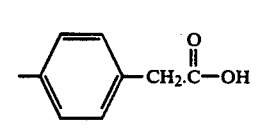 |
| 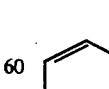 | 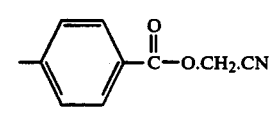 |
| 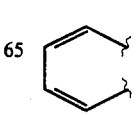 | 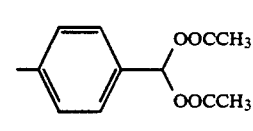 |

-continued

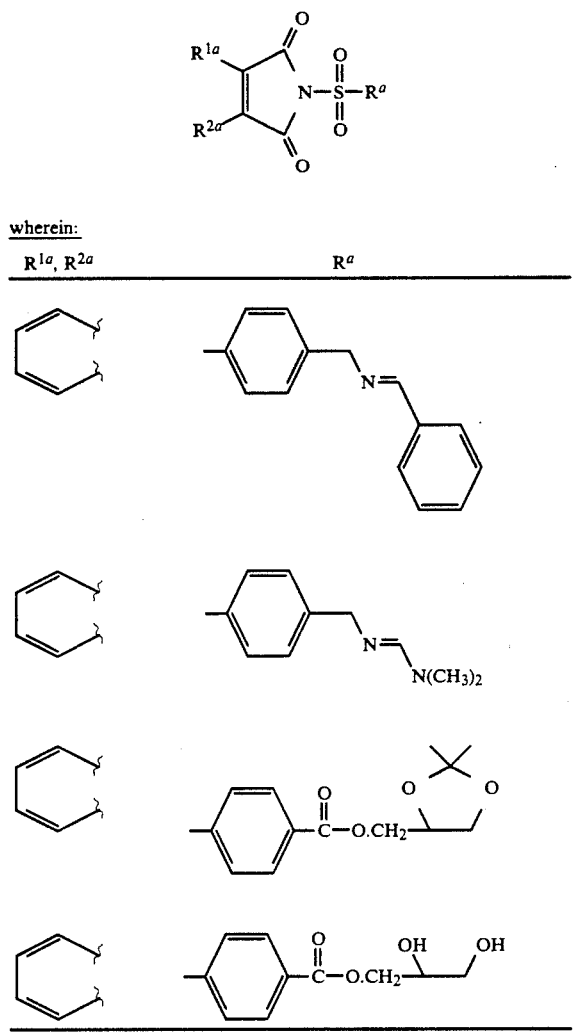

wherein:

| $R^{1a}, R^{2a}$ | $R^a$ |

3. A compound of claim 1 wherein $R^a$ is phenyl or naphthyl, substituted by 1-5 groups $R^{4a}$.

4. A compound of claim 3 wherein $R^{4a}$ is Y-substituted alkyl, alkylamino, dialkylamino or alkoxycarbonyl.

5. A compound of claim 4 wherein Y is halogeno, benzyloxycarbonyl or triphenylphosphonium.

6. A compound of claim 1 wherein q=0.

7. A pharmaceutical composition comprising a PDGF inhibitory amount of a compound of claim 1 in a pharmaceutically acceptable carrier.

8. A method of inhibiting the binding of platelet-derived growth factor by treating a mammal in need of such treatment with a inhibitory effective dose of a compound of the formula

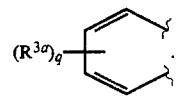

or a pharmaceutically acceptable addition salt thereof, wherein p is 0, 1, 2, 3, 4, 5, or 6 and R is hydrogen or an aryl group substituted by 1-5 substitutents $R^4$, provided that R is not hydrogen when p=0;

$R^1$ and $R^2$ taken together comprise a fused ring of the formula $$(R^{3a})_q \text{—} \bigcirc$$

q is 0, 1, 2, 3 or 4;

X and $R^3$ are independently selected from the group consisting of hydrogen, halogeno, hydroxy, $C_1$-$C_8$ alkyl, $C_1$-$C_8$ alkenyl, $C_1$-$C_8$ alkoxy, aryloxy, amino, alkylamino, dialkylamino, arylamino, diarylamino, trialkylammonium, thio, —$S(O)_2R^6$, —$S(O)_mR^7$, —$SO_3$, nitro, —$NHS(O)_2$alkyl, carboxyl, alkoxycarbonyl, carboxamido, N-alkylcarboxamido, N,N-dialkylcarboxamido, alkylcarbonylamino, arylcarbonylamino, alkylaminocarbonyloxy, alkoxycarbonyloxyl, alkylcarbonyloxy, trifluoromethyl, cyano, aryl, and substituted aryl, wherein the substitutents are 1-5 groups $R^4$;

and wherein the $R^4$ substituents are independently selected from the group consisting of hydrogen, halogeno, $C_1$-$C_8$ alkenyl, $C_1$-$C_8$ alkynyl, hydroxy, $C_1$-$C_8$ alkyl, Y-substituted alkyl, $C_1$-$C_8$ alkoxy, aryloxy, amino, alkylamino, dialkylamino, arylamino, diarylamino, trialkylammonium, thio, —$SO_2R^6$, —$S(O)_mR^7$, —$SO_3$, nitro, carboxy, alkoxycarbonyl, benzyloxycarbonyl, alkenyloxycarbonyl, carboxamido, N-phthalimido, cyanoalkoxycarbonyl, carboxyalkoxycarbonyl, benzyloxycarbonylalkoxycarbonyl, N-alkylcarboxamido, N,N-dialkylcarboxamido, trifluoromethyl, cyano and aryl;

Y is selected from the group consisting of halogeno, trialkylammonium, amino, carboxy, pyridinium, triarylphosphonium, benzyloxycarbonyl, hexamethylenetetraminium, —N=CH—alkyl, —N=CH—aryl and —N=CH—N(alkyl)$_2$;

$R^6$ is amino, arylamino, alkylamino or dialkylamino;

$R^7$ is $C_1$-$C_8$ alkyl or aryl; and m is 0, 1 or 2.

9. A method claim 8 wherein the compound has the structural formula

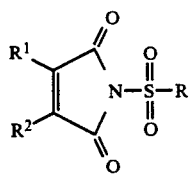
wherein:
| R¹, R² | R |
|---|---|
|  | 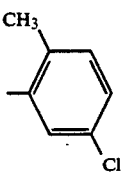 |
|  | 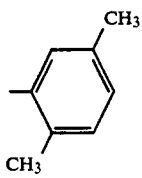 |
|  | 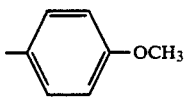 |
|  | 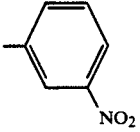 |
|  | 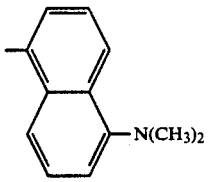 |
|  | 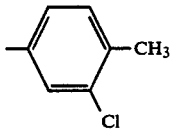 |
|  | 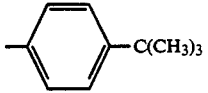 |
|  | 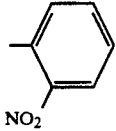 |

-continued
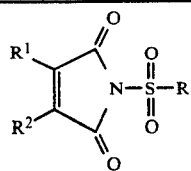
wherein:
| $R^1, R^2$ | R |
|---|---|
|  | 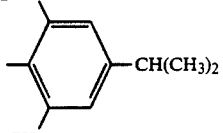 |
|  | 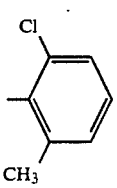 |
|  | 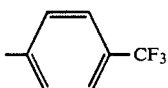 |
|  | 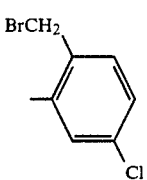 |
|  | 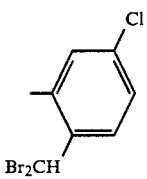 |
|  | 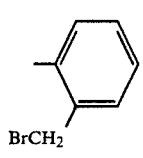 |
|  | 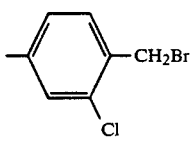 |
|  | 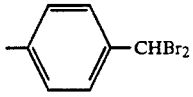 |
|  | 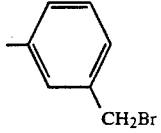 |

-continued
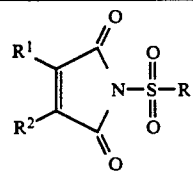
wherein:
| $R^1, R^2$ | R |
|---|---|
| 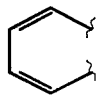 | 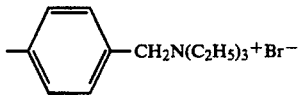 |
| 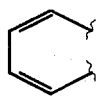 | 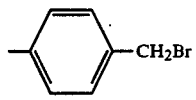 |
| 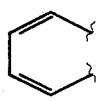 | 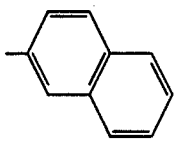 |
| 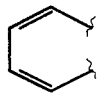 | 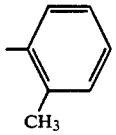 |
| 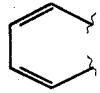 | 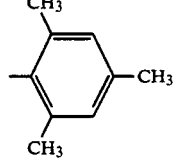 |
| 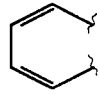 | 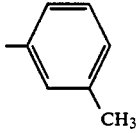 |
| 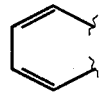 |  |
| 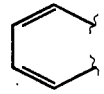 | 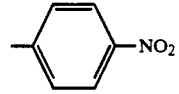 |
| 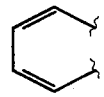 | 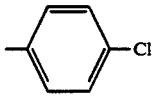 |
| 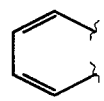 | 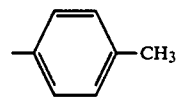 |

-continued
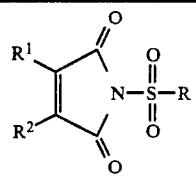
wherein:
| R¹, R² | R |
|---|---|
| 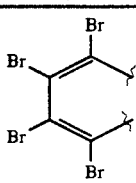 | 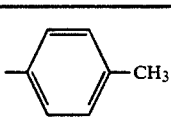 |
| 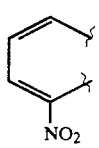 | 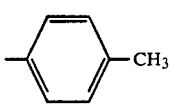 |
| 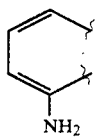 | 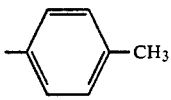 |
|  | 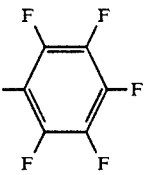 |
|  | 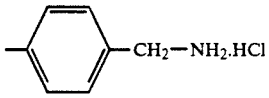 |
|  | 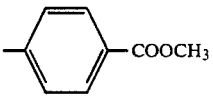 |
|  | 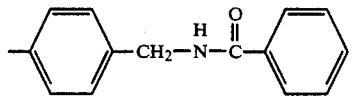 |
|  | 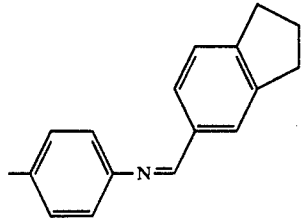 |
|  | 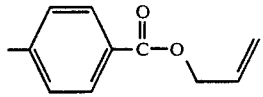 |

-continued
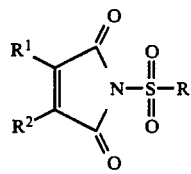
wherein:
| $R^1, R^2$ | R |
|---|---|
|  | 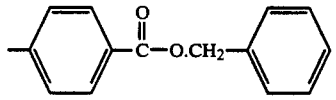 |
|  | 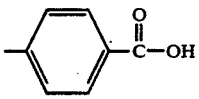 |
|  | 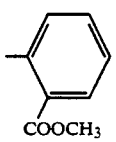 |
|  | 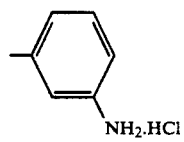 |
|  | 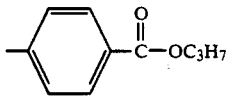 |
|  | 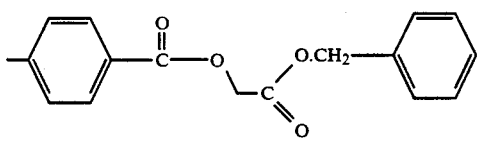 |
|  | 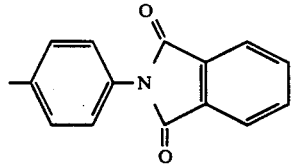 |
|  | 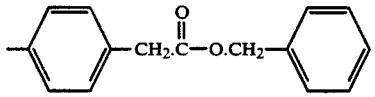 |
|  | 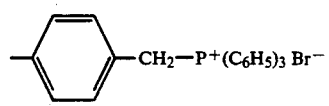 |
|  | 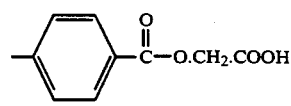 |

-continued

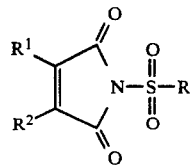

wherein:

| $R^1, R^2$ | R |
|---|---|
| (phenyl) | -C6H4-CH2.C(=O)-OH |
| (phenyl) | -C6H4-C(=O)-O.CH2.CN |
| (phenyl) | -C6H4-CH(OOCCH3)2 |
| (phenyl) | -C6H4-CH=N-CH2-C6H5 |
| (phenyl) | -C6H4-CH=N-N(CH3)2 |
| (phenyl) | -C6H4-C(=O)-O.CH2-(isopropylidene dioxy) |
| (phenyl) | -C6H4-C(=O)-O.CH2-CH(OH)-CH2OH |
| (benzoylamino-phenyl) | -C6H4-CH3 |

10. A method of treating atherosclerosis, cancer, retinal detachment, pulmonary fibrosis, arthritis, psoriasis, glomerulonephritis, and restenosis following angioplasty or vascular surgery, in a mammal in need of such treatment, comprising administering an effect amount of a composition of claim 7.

11. A method of inhibiting PDGF comprising administering an effective amount of a composition of claim 7 to a mammal in need of such treatment.

12. A method of claim 8 wherein the compound has the structural formula

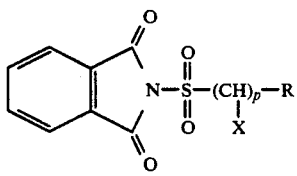
wherein
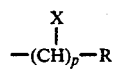
is selected from the group consisting of —CH$_2$—C$_6$H$_5$, —(CH$_2$)$_2$—C$_6$H$_5$, —(CH$_2$)$_3$—C$_6$H$_5$, —CH$_3$, —C$_4$H$_9$, —C$_{12}$H$_{15}$, 3-chloropropan-1-yl or
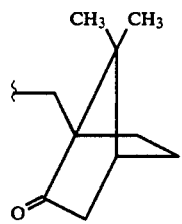
* * * * *

UNITED STATES PATENT AND TRADEMARK OFFICE
CERTIFICATE OF CORRECTION

PATENT NO. : 5,238,950
DATED : AUGUST 24, 1993
INVENTOR(S) : CLADER, ET AL.

It is certified that error appears in the above-identified patent and that said Letters Patent is hereby corrected as shown below:

In claim 1, at column 23, line 63, delete "pyridinium".

In claim 1, at column 23, lines 64-65, delete "hexamethylenetetraminium".

In claim 8, at column 28, line 20, delete "$(R^{3a})_q-$" and insert therefore --$(R^3)_q-$ --.

Signed and Sealed this

Tenth Day of May, 1994

Attest:

BRUCE LEHMAN

*Attesting Officer*    *Commissioner of Patents and Trademarks*